United States Patent
Spagnoli et al.

(10) Patent No.: US 7,964,208 B2
(45) Date of Patent: *Jun. 21, 2011

(54) SYSTEM AND METHODS OF MAINTAINING SPACE FOR AUGMENTATION OF THE ALVEOLAR RIDGE

(75) Inventors: Daniel B. Spagnoli, Charlotte, NC (US); Todd A. Mobley, Collierville, TN (US); Jeffrey L. Scifert, Arlington, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 132 days.

This patent is subject to a terminal disclaimer.

(21) Appl. No.: 12/392,163

(22) Filed: Feb. 25, 2009

(65) Prior Publication Data

US 2010/0217331 A1    Aug. 26, 2010

(51) Int. Cl.
*A61B 17/58* (2006.01)
(52) U.S. Cl. ............ 424/423; 606/60; 606/270; 606/65; 514/8.8; 514/16.7
(58) Field of Classification Search .................. None
See application file for complete search history.

(56) References Cited

U.S. PATENT DOCUMENTS

| | | | |
|---|---|---|---|
| 3,579,831 A | 5/1971 | Stevens et al. | |
| 5,176,680 A | 1/1993 | Vignaud et al. | |
| 5,201,733 A | 4/1993 | Etheredge | |
| 5,755,575 A | 5/1998 | Biggs | |
| 5,839,899 A | 11/1998 | Robinson | |
| 5,888,034 A * | 3/1999 | Greenberg | 408/115 R |
| 5,899,940 A | 5/1999 | Carchidi et al. | |
| 5,971,985 A | 10/1999 | Carchidi et al. | |
| 5,972,368 A | 10/1999 | McKay | |
| 6,120,292 A | 9/2000 | Buser et al. | |
| 6,146,420 A | 11/2000 | McKay | |
| 6,149,653 A * | 11/2000 | Deslauriers | 606/232 |
| 6,290,500 B1 | 9/2001 | Morgan et al. | |
| 6,325,627 B1 | 12/2001 | Ashman | |
| 6,394,807 B2 | 5/2002 | Robinson | |
| 6,402,518 B1 | 6/2002 | Ashman | |
| 6,722,884 B2 | 4/2004 | Ashman | |
| 6,761,738 B1 | 7/2004 | Boyd | |
| 6,949,100 B1 | 9/2005 | Venturini | |
| 7,074,426 B2 | 7/2006 | Kochinke | |
| 7,090,493 B2 | 8/2006 | Chang | |

(Continued)

FOREIGN PATENT DOCUMENTS

DE    4329788 B4    5/2007

(Continued)

OTHER PUBLICATIONS

Ace Bone Grafting and Ridge Split Augmentation Catalog, 2004; see p. 4.

(Continued)

*Primary Examiner* — Elizabeth C. Kemmerer

(57) ABSTRACT

An implantable screw for maintaining space during bone grafting procedures is provided, where the screw has a highly-polished contoured head having a region adapted to support soft tissue, a threaded shaft and a tip adapted to penetrate bone tissue. Also provided, a device combining multiple implantable screws in series in order to increase the available space to grow new bone and a method for implanting the implantable screw. The implantable screws provided may be used in conjunction with bone graft materials and are removable once a desired amount of new bone is generated.

20 Claims, 2 Drawing Sheets

U.S. PATENT DOCUMENTS

| | | | |
|---|---|---|---|
| 7,166,570 B2 | 1/2007 | Hunter et al. | |
| 7,309,232 B2 | 12/2007 | Rutherford et al. | |
| 7,322,978 B2 | 1/2008 | West | |
| 2008/0004623 A1 | 1/2008 | Ferrante et al. | |
| 2008/0095709 A1 | 4/2008 | Ella | |
| 2010/0023064 A1* | 1/2010 | Brunger et al. | 606/308 |

FOREIGN PATENT DOCUMENTS

| | | |
|---|---|---|
| EP | 1688103 A1 | 9/2006 |
| JP | 07-328041 A | 12/1995 |
| KR | 10-0613756 B1 | 8/2006 |

OTHER PUBLICATIONS

Kao, et al.; Tissue Engineering for Periodontal Regeneration; CDA Journal, vol. 33, No. 3, pp. 205-215—Mar. 2005.

Rose; Bone Grafts and Growth and Differentiation Factors for Regenerative Therapy: A Review; Prac. Proc. Aesthet. Dent. 2001; 13(9):725-734 and 736.

U.S. Appl. No. 12/179,471, filed Jul. 24, 2008.

International Search Report and Written Opinion for US Application PCT/US2010/025075 mailed on Nov. 12, 2010.

* cited by examiner

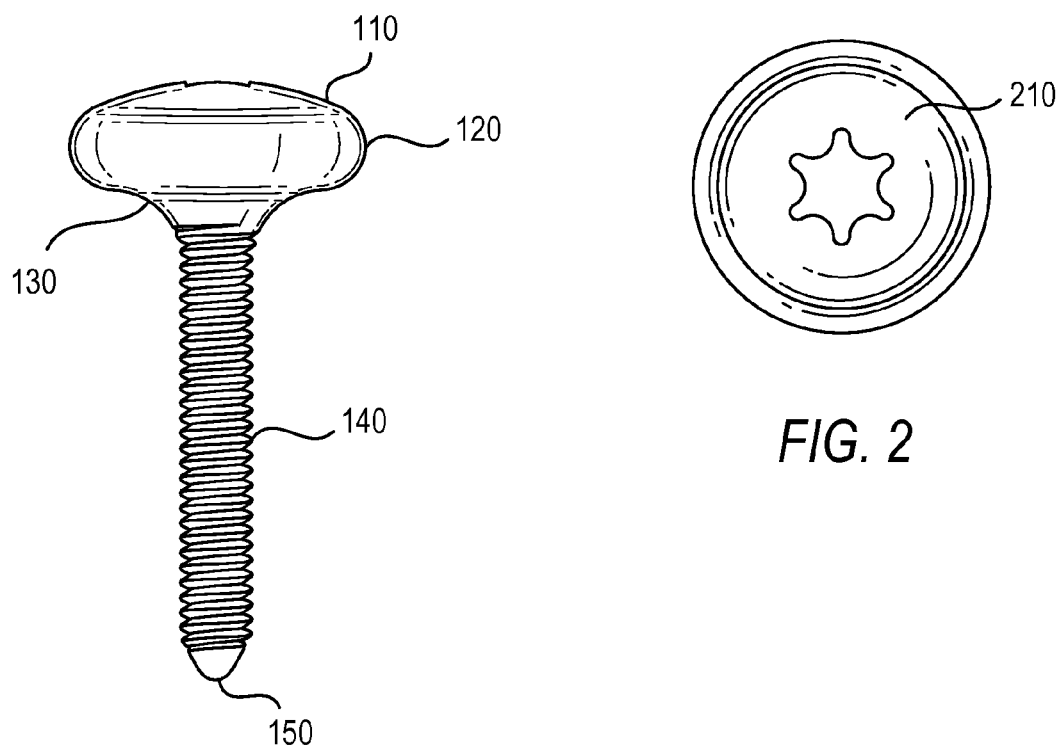
FIG. 1
FIG. 2
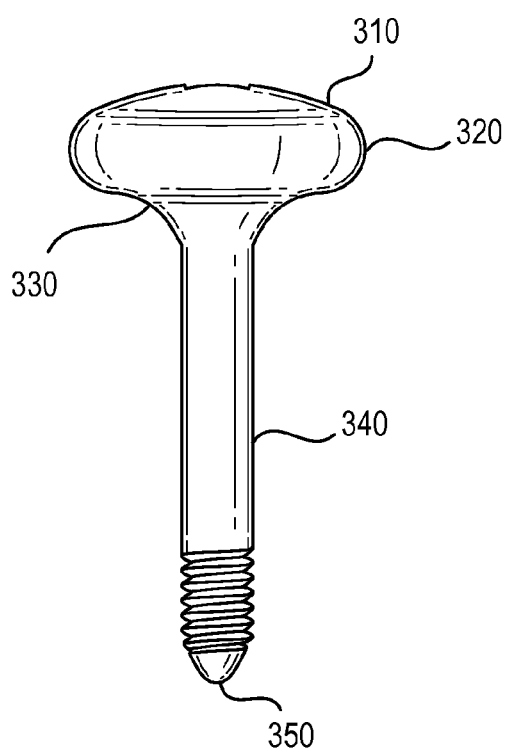
FIG. 3

SYSTEM AND METHODS OF MAINTAINING SPACE FOR AUGMENTATION OF THE ALVEOLAR RIDGE

BACKGROUND

The successful use of dental implants has long been known and is well documented in the field. Despite successful dental implant procedures through the years, the success of the placement of a dental implant is limited by the quality and quantity of existing bone of a given patient. Due to the destructive nature of dentures to the underlying jawbone the amount of bone in many people is very limited for the placement of dental implants.

Furthermore, atrophy of the jawbone can occur when the bone is not subjected to occlusal loads. Therefore, atrophy may occur over time when a tooth is not replaced with a dental implant. As a result, when a person has been partially edentulous for a long period of time, they may suffer from an atrophic alveolar ridge that is not capable of securely supporting a dental implant. The deterioration of the alveolar ridge has severe consequences, including reducing one's ability to masticate and compromising aesthetics.

In this situation, bone grafting has become an essential element for the successful treatment of those who do not have enough bone for dental implants. There are many known methods of bone grafting. Bone grafting procedures may incorporate bone graft material in order to stimulate bone growth. As viable exemplary methods, blocks of hip bone have been affixed to the jaw and freeze-dried demineralized bone protein has been used as a stimulant to cause the patient's bone cells to become active and lay down new bone onto the existing bone areas and into the new bone graft areas. Through experience and research, it has become evident that, for bone grafting to be successful, it must be given an isolated space to grow, protected from muscular pressure, tissue impingement and forces of mastication. In order to create this space, fabric-like membranes or barriers have been used over a bony defect. Although this barrier creates an isolated space from the invasion of connective tissue cells into the bony defect or bone graft area, it does not create a protected space from chewing forces or tissue pressure. It is necessary to protect the growing bone from all aspects of potential harm. Therefore, in many instances the space is created and maintained utilizing dental implants and supports including a tenting-type support screw.

SUMMARY

A new implantable screw is provided for maintaining space during bone grafting procedures. This screw comprises a contoured head having a highly-polished, machined surface, a region adapted to support soft tissue and to shield the graft area from compressive forces, and a curved under surface to increase capacity for bone growth. The head may vary in size; typically the head is in the range of about 3 mm to about 7 mm. The screw further comprises a threaded shaft used to anchor the screw in the existing jawbone. The size of the shaft may also vary. The shaft may have an outer diameter of 2.0 mm or less and an inner diameter of 1.8 mm or less, where the inner diameter is always less than the outer diameter. The tip of the screw is adaptable to penetrate bone tissue. The implantable screw is removable once a desired amount of new host bone has been generated.

Another embodiment provides an implantable device for maintaining space during bone grafting procedures in a patient in need of such treatment. The implantable device comprises at least a first screw and a second screw. Each screw has a contoured head having a highly-polished, machined surface, a region adapted to support soft tissue and to shield the graft area from compressive forces, and a curved under surface to increase capacity for bone growth. Each screw further provides a threaded shaft for anchoring the screw in the bone and a tip adapted to penetrate bone tissue. In some embodiments the head of the first screw is adjacent to the head of the second screw to increase the tenting area. The implantable screw is removable once a desired amount of new host bone has been generated.

Additionally, a method of using an implantable screw device for oral bone grafting procedures is provided. The method comprises implanting a device comprising at least one implantable screw into the jawbone. The implantable screw comprises a contoured head having a highly-polished, machined surface, a region adapted to support soft tissue and to shield the graft area from compressive forces, and a cured under surface to increase capacity for bone growth. The head may range in size, but is typically between about 3 mm to about 7 mm. The shaft of the screw is threaded for anchoring the screw in the bone. The shaft of the screw has an outer diameter of 2.0 mm or less and an inner diameter of the shaft is 1.8 mm or less, and the inner diameter is always less than the outer diameter. The tip of the screw is adapted to penetrate bone tissue. The method further comprises incorporating a bone growth material around the device to stimulate bone growth and removing the device once a desired amount of new host bone has been generated.

Additional features and advantages of various embodiments will be set forth in part in the description that follows, and in part will be apparent from the description or figures, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

FIG. 1: illustrates an implantable screw including a contoured head, a threaded shaft and a tip adapted to penetrate bone tissue.

FIG. 2: illustrates the top view of the contoured head of an implantable screw.

FIG. 3: illustrates an implantable screw including a contoured head, a partially threaded shaft and a tip adapted to penetrate bone tissue.

Figure 4:
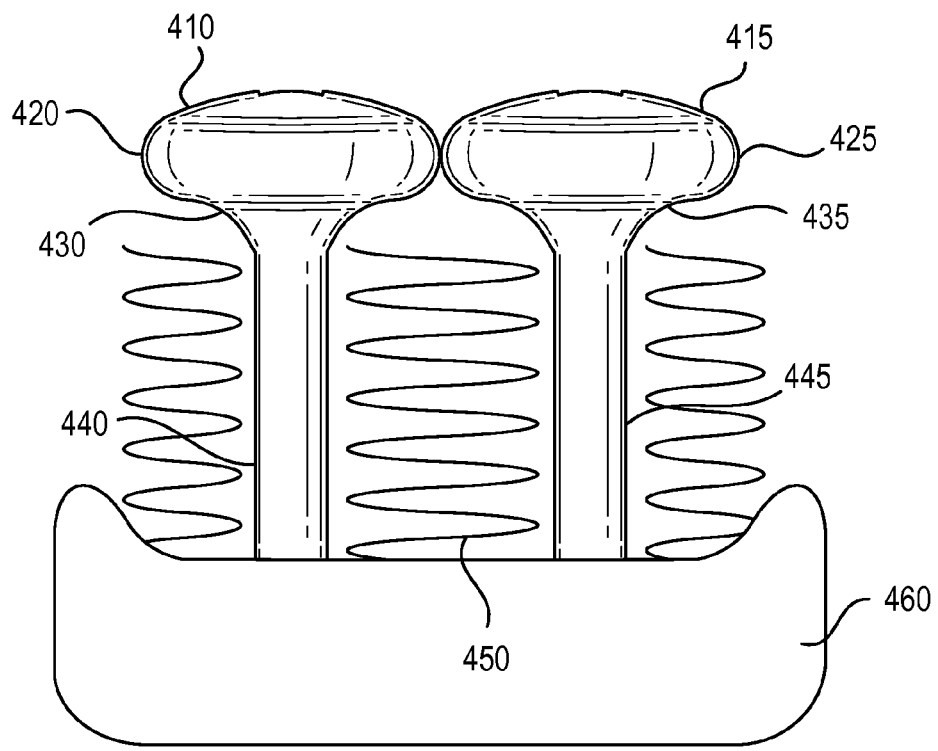
FIG. 4: illustrates an implantable device including two screws, each having a contoured head, a shaft and a tip engaged in bone.

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

For the purposes of this specification and appended claims, unless otherwise indicated, all numbers expressing quantities of ingredients, percentages or proportions of materials, and other numerical values used in the specification and claims, are to be understood as being modified in all instances by the term "about." Accordingly, unless indicated to the contrary, the numerical parameters set forth in the following specification and attached claims are approximations that may vary depending upon the desired properties to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements. Moreover, all ranges disclosed herein are to be understood to encompass any and all subranges subsumed therein. For example, a range of "1 to 10" includes any and all subranges between (and including) the minimum value of 1 and the maximum value of 10, that is, any and all subranges having a minimum value of equal to or greater than 1 and a maximum value of equal to or less than 10, e.g., 5.5 to 10.

It is noted that, as used in this specification and the appended claims, the singular forms "a," "an," and "the," include plural referents unless expressly and unequivocally limited to one referent. Thus, for example, reference to "an implantable device" includes one, two, three or more implantable devices.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents, which may be included within the invention as defined by the appended claims.

Provided herein is an implantable screw for maintaining space during bone grafting procedures in a patient in need of such treatment. As an illustrative example, not a limitation, the screw can be used to treat orofacial diseases, or used in oral and maxillofacial surgical procedures for alveolar ridge preservation and/or augmentation as well as other surgical procedures.

The screw can be implanted into tissues within orofacial tissue, which includes tissue sites located within the oral cavity. Such tissue includes by way of illustration and not limitation, periodontal tissue such as the periodontium; periodontal ligaments; bone tissue at the end of an infected tooth, inside the tooth or within the bone cavity such as may be present after an apicoectomy or tooth extraction; endodontic tissue; bone tissue surrounding an implant fixture; jaw tissue such as the temporomandibular joint, the temporalis muscle, the temporal bone the masseter muscle and the mandible; tissue affected by surgery, e.g. tonsillectomy; and so forth.

The term "orofacial disease" is intended to encompass diseases within the orofacial environment, as well as diseases that originate in the orofacial environment. The term "orofacial disease" is intended to include, by way of illustration and not limitation, acute and chronic inflammation, including chronic inflammation of the tissue (including host response reactions) to stop the process of the on-going tissue decay; infection; pain and related inflammatory and other complications of mechanical teeth cleaning (including root planning and scaling), all periodontal surgical procedures, and other surgical procedures such as an apicoectomy or root canal, procedures done to facilitate tooth movement such as orthodontia; repair damage to periodontal ligament, bone and other tissues that has been caused by periodontal disease; cranomandibular disease which produces facial, head, ear and jaw pain, examples of which include temporomandibular joint syndrome; cosmetic and plastic surgery to reconstruct and rebuild facial features after accidents or other deformations or the like. The term "orofacial disease" is intended to encompass diseases within the orofacial environment, as well as diseases that originate in the orofacial environment.

Treating or treatment of a disease refers to executing a protocol, which may include implanting one or more implantable screws to a patient (human or otherwise), in an effort to alleviate signs or symptoms of the disease. Alleviation can occur prior to signs or symptoms of the disease appearing, as well as after their appearance. Thus, "treating" or "treatment" includes "preventing" or "prevention" of disease. In addition, "treating" or "treatment" does not require complete alleviation of signs or symptoms, does not require a cure, and specifically includes protocols that have only a marginal effect on the patient.

In some embodiments, the implantable screw disclosed herein allows surgeons to utilize existing bone graft materials to treat bony defects in which space maintenance is crucial for success, but in which limited options for maintaining that space currently exist. The screw can be used for alveolar ridge augmentation, where increase in volume and bone is desired. An alveolar ridge (also known as the alveolar process) comprises the portion of bone in the upper jaw (the maxilla) or the lower jaw (the mandible) that surrounds and supports the teeth. Often, these areas do not contain enough native bone for dental implant placement or stabilization, and thus, the volume of bone needs to be increased.

In various embodiments, the implantable screw provides space between the bone and gingival. Gingival tissue includes part of the soft tissue lining of the mouth. It surrounds the teeth and provides a seal around them. Compared with the soft tissue linings of the lips and cheeks, most of the gingiva are tightly bound to the underlying bone and are designed to resist the friction of food passing over them. Thus the implantable screw supports the gingival so that bone can regenerate and restore the proper jaw structure for proper aesthetics and for dental implant-borne restoration.

The implantable screw is designed to have a larger head and a smaller shaft as compared to other screws used for tenting. The head is contoured such that the smooth rounded edges provide an interface that will not be harmful to the overlying gingival or mucosal tissue. Further, the implantable screw provides a head having a curved under surface to provide additional space between the bone and the gingival, allowing for placement of bone graft material and bone growth adequate for restoration of proper jaw structure for proper aesthetics and for dental implant-borne restorations. Thus, the implantable screw provides an attractive option to surgeons seeking space maintenance materials to use with bone grafting and bone regenerative products.

The figures and corresponding descriptions below are not meant to limit the disclosure in any way; embodiments illustrated and described in connection with any one figure may be used in conjunction with embodiments illustrated and described in connection with any other figure unless otherwise expressly provided.

FIGS. 1-5 illustrate various embodiments of tenting screws for use as implantable devices generally referred to by the reference numerals 110-580, respectively. Similar reference numbers will be used throughout the drawings to refer to similar portions of similar parts.

FIG. 1 illustrates an implantable screw for temporarily maintaining or creating space during bone grafting in certain dental regenerative procedures. In various embodiments the implantable screw comprises a contoured head 110, a threaded shaft 140, and a tip 150 adapted to penetrate bone tissue.

The head of the screw has smooth, contoured edges 120 to support the interface between the gingival and the screw head, minimizing the likelihood of dehiscence or piercing of the soft tissue in the jaw region. The contoured head of the implantable screw shields the graft region from compressive forces providing a protected area for bone growth. Further, the surface of the contoured head is highly-polished using known methods such as buffing so that the finished surface is smooth and grainless. The highly-polished surface allows the screw to be resistant to plaque and tarter build-up. Machining operations such as CNC or lathe are also used to manufacture the surface and geometry of the screws during production.

In many embodiments, the contoured head also provides a curved under surface 130, or an "umbrella shape" to ensure sufficient space is maintained or created for grafting of the alveolar ridge. Approximately 0 mm to 20 mm of space should be maintained between the native bone and the tented soft tissue, allowing ample space for new bone growth. A graft may be used to either induce new bone formation and/or serve as an osteoconductive scaffold as bone forms in the space provided.

The head may be provided in various sizes. The head size is large to provide increased area for bone growth and to minimize dehiscence or piercing of the surrounding tissue. Further a larger diameter head acts to distribute fixation forces over a wider area, improving stability and lessening the likelihood that head will penetrate of split bone grafts comprised of natural materials. Typically the head will range in diameter size between about 3 mm and about 7 mm, providing 1 mm incremental increases. Typical head sizes are 3 mm, 4 mm, 5 mm, 6 mm or 7 mm.

The shaft of the implantable screw allows the user (e.g., surgeon, dentist or other health care provider) to anchor the screw in the bone. In some embodiments the shaft of the implantable screw may be fully threaded, i.e., from tip to head. The threading pitch of the shaft is such that primary stability of the screw may be attained after engagement of about 3 mm to about 4 mm of bone.

The screw shaft has a smaller than normal diameter to increase the available space for bone growth and to minimize the impact on new host bone upon removal of the screw. Various embodiments provide a shaft having an outer diameter of about 2.0 mm or less and an inner diameter of about 1.8 mm or less. In every case, the inner diameter will be less than the outer diameter. Typically, the outer diameter will be about 1.4 mm and the inner diameter will be about 1.2 mm.

The length of the shaft is also variable depending on the requirements. The shaft length may range between about 8 mm and about 17 mm, providing 1 mm incremental increases. Typical lengths provided in various embodiments include, 8 mm, 9 mm, 10 mm, 11 mm, 12 mm, 13 mm, 14 mm, 15 mm, 16 mm, and 17 mm.

The tip of the implantable screw is adapted to penetrate bone tissue. The tip may be of any shape that is commonly used for such purpose. The screw may be either self-drilling, or may be adapted for self-tapping and self-drilling after minimal pilot.

In some embodiments, the screw may be positioned for use in a variety of procedures including those procedures requiring vertical or lateral augmentation of the alveolar ridge.

Once a desired amount of new host bone has been generated, the implantable screw is removable. The dimensions of the head and shaft are such that the impact and potential damage to the new bone upon removal is minimized. The removal of the tenting screw provides a region of new bone ideally sufficient to support the placement of an oral implant if desired. The amount of desired new host bone is dependent on the specific purpose of the procedure. In some embodiments the implant may be inserted into the same space left vacant by the removal of the implantable tenting screw.

FIG. 2 illustrates an exemplary top view of the contoured head of an implantable screw. In various embodiments, the head of the screw may have one or more recessed and/or projections 210 that may be any size and shape e.g., straight, flat-sided shape, an elliptical shape, bi-concave shape, square shape, or any other protruding or recessed shape which provides sufficient implantation tool-engaging end strength and drive purchase to allow transmission of insertional torque without breaking or otherwise damaging the implantable screw. Typically a screw can be turned by hand, drill or other dental instrument designed to turn the screw clockwise or counterclockwise as needed so that the tip can penetrate the bone.

Implantation tools include, but are not limited to a driver, wrench, spanner, screwdriver, or other turning tool, and the like that can engage the implantable device. The implantation tool may be used manually (e.g., turnable by hand) or by an automatic device (e.g., using a drill, power driver, etc.). Exemplary embodiments may employ the use of a torx or star drill.

In another exemplary embodiment, FIG. 3 illustrates an implantable screw as previously described, having a contoured head 310, with smooth, contoured edges 320 and a curved under surface 330. The implantable screw further comprises a shaft 340 and tip 350. In some embodiments the shaft of the screw is threaded on the apical or coronal regions of the screw so the entire length of the shaft is threaded or less than the entire length of the shaft is threaded. Typically the threading initiates at the tip of the screw and proceeds up toward the head providing at least enough threading to ensure stabilization of the screw. In various embodiments, the thread pitch is sufficient to stabilize the screw after engaging about 3 mm to about 4 mm of bone.

In some embodiments, multiple implantable screws may be used for temporary space maintenance during bone grafting procedures. FIG. 4 illustrates an exemplary embodiment of an implantable device comprising two implantable screws implanted adjacent to each other. The first screw comprises a head 410, a threaded shaft 440 and a tip (not visible) to anchor the screw into the jawbone 460. The second screw also comprises a head 415, a threaded shaft 445 and a tip (not visible) to anchor the screw into the jawbone.

The head of the first screw has smooth, contoured edges 420 and a curved under surface 430. Similarly, the head of the second screw comprises smooth, contoured edges 425 and a curved under surface 435. The contoured edges help to minimize dehiscence or piercing of the surrounding soft tissue and the curved under surface increases the area for bone growth. In embodiments where the screws are implanted in series, each screw may be positioned such that each screw head is adjacent to the next screw head. The adjacent positioning of each successive screw head allows a larger area of the graft region to be protected and increases the area available for growing new bone. The size may vary depending on the available space and what the procedure necessitates.

The head of each screw is large to further maximize the area of the protected graph region. Each screw head may vary in diameter size. Typically a screw head may have a diameter of either 3 mm, 4 mm, 5 mm, 6 mm or 7 mm. An implantable device having multiple screws may incorporate screws where the diameter of each screw head is the same size (e.g., the diameter of the head of each a first screw and a second screw is 4 mm), a different size (e.g., the diameter of the head of a first screw is 4 mm and the the diameter of the head of a second screw is 6 mm), or a combination of various sizes (e.g., the diameter of the head of a first screw is 4 mm, a second screw is 6 mm and a third screw is 4 mm). The size may vary depending on the available space and what the procedure necessitates.

The shaft of each implantable screw may be either fully or partially threaded such that the screw may be anchored into the jaw. In the exemplary embodiment, stability of the screw will be attained after about 3 mm to about 4 mm of engagement with the jawbone.

The shaft of each implantable screw may also range in diameter and length. The diameter of the shaft is small in order to leave more room for new bone as well as to minimize the amount of bone impacted upon removal. Some embodiments provide that the outer diameter of each implantable screw is 2.0 mm or less while the inner diameter is 1.8 mm or less. In every case, the inner diameter is less than the outer diameter. Further the length of the shaft may vary in the range of 8 mm to 17 mm. Each screw implanted in the implantable device may have a shaft of the same diameter or the same length of subsequent screws, a different diameter or a different length of subsequent screws, or any combination thereof.

In some embodiments, bone growth material 450 is incorporated to encourage the development of new bone. Bone growth materials for stimulating bone growth may be artificial, synthetic, natural, or natural substitutes. Bone growth materials may be provided to the socket in a variety of ways, including by way of example, coating the screw with the bone growth material or injection of a bone growth agent into the socket. The type of growth agent and the quantity needed will depend on the patient and the type of procedure required.

In some embodiments an individual screw or combination of multiple screws may be used simultaneously to tent space for bone growth as well to a fixate tissue scaffolds such as membranes, meshes, sponges or the like. The screw can be passed through the scaffold, or in some embodiments, the tissue scaffold can be packed around the screw. The tissue scaffolds provides a matrix for the cells to guide the process of tissue formation in vivo in three dimensions. The morphology of the scaffold guides cell migration and cells are able to migrate into or over the scaffold, respectively. The cells then are able to proliferate and synthesize new tissue (e.g., bone). In some embodiments, one or more tissue scaffolds are stacked on or intermixed with each other.

In some embodiments, the tissue scaffold may comprise natural and/or synthetic material. For example, the tissue scaffold may comprise poly(alpha-hydroxy acids), poly(lactide-co-glycolide) (PLGA), polylactide (PLA), polyglycolide (PG), polyethylene glycol (PEG) conjugates of poly (alpha-hydroxy acids), polyorthoesters (POE), ultra high molecular weight porous polyethylene, polyaspirins, polyphosphagenes, collagen, hydrolyzed collagen, gelatin, hydrolyzed gelatin, fractions of hydrolyzed gelatin, elastin, starch, pre-gelatinized starch, hyaluronic acid, chitosan, alginate, albumin, fibrin, vitamin E analogs, such as alpha tocopheryl acetate, d-alpha tocopheryl succinate, D,L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate), polydioxanone, methylmethacrylate (MMA), MMA and N-vinylpyyrolidone, polyamide, oxycellulose, copolymer of glycolic acid and trimethylene carbonate, polyesteramides, polyetheretherkeone, polymethylmethacrylate, or combinations thereof.

In some embodiments, the tissue scaffold comprises collagen. Exemplary collagens include human or non-human (bovine, ovine, and/or porcine), as well as recombinant collagen or combinations thereof. Examples of suitable collagen include, but are not limited to, human collagen type I, human collagen type II, human collagen type III, human collagen type IV, human collagen type V, human collagen type VI, human collagen type VII, human collagen type VIII, human collagen type IX, human collagen type X, human collagen type XI, human collagen type XII, human collagen type XIII, human collagen type XIV, human collagen type XV, human collagen type XVI, human collagen type XVII, human collagen type XVIII, human collagen type XIX, human collagen type XXI, human collagen type XXII, human collagen type XXIII, human collagen type XXIV, human collagen type XXV, human collagen type XXVI, human collagen type XXVII, and human collagen type XXVIII, or combinations thereof. Collagen further may comprise hetero- and homo-trimers of any of the above-recited collagen types. In some embodiments, the collagen comprises hetero- or homo-trimers of human collagen type I, human collagen type II, human collagen type III, or combinations thereof.

In some embodiments, the tissue scaffold may be seeded with harvested bone cells and/or bone tissue, such as for example, cortical bone, autogenous bone, allogenic bones and/or xenogenic bone. For example, before insertion into the target tissue site, the tissue scaffold can be wetted with the graft bone tissue/cells, usually with bone tissue/cells aspirated from the patient, at a ratio of about 3:1, 2:1, 1:1, 1:3 or 1:2 by volume. The bone tissue/cells are permitted to soak into the scaffolding provided, and the scaffolding may be kneaded by hand, thereby obtaining a pliable consistency that may subsequently be packed into the defect. In some embodiments, the tissue scaffold provides a malleable, non-water soluble carrier that permits accurate placement and retention at the implantation site.

The shape of the tissue scaffold may be tailored to the site at which it is to be situated. For example, it may be in the shape of a morsel, a plug, a pin, a peg, a cylinder, a block, a wedge, a sheet, etc.

The tissue scaffolds may be used to initiate bone growth in the particular area. Exemplary, non-limiting, tissue scaffolds suitable for use with the screw include, ceramics, bone morphogenetic protein (BMP) in combination with ceramic-collagen composites, a collagen sponge that contains recombinant human bone morphogenetic protein (rhBMP-2), and calcium phosphate-based cements. Tissue scaffolds, such as collagen sponges containing rhBMP-2 are available from Medtronic Sofamor Danek.

Figure 5:
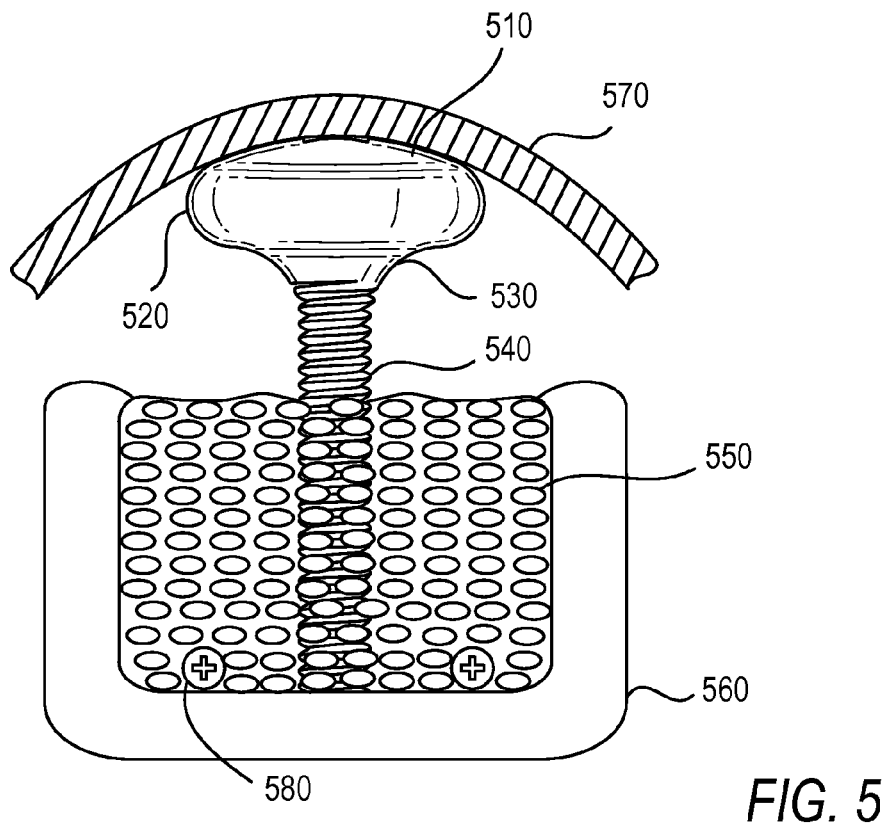
FIG. 5: illustrates of an implantable screw engaged in mesh and bone.

FIG. 5 is an exemplary embodiment illustrating an implantable screw being used for tenting as well as to secure mesh. The exemplary implantable screw has a contoured head 510, a threaded shaft 540 and a tip (not visible). The contoured head supports the tenting of soft tissue 570, while the smooth, contoured edges 520 minimizes the potential for damage to the soft tissue. The curved under surface 530 provides increased space for the placement of the mesh 550 and for growing new bone.

In the illustrated embodiment, the tip of the screw is passed through the mesh, preferably allowing the mesh to be captured by the screw threads under the head of the screw to help hold the mesh above the bone graft site before being anchored into the jawbone 560. When sufficient bone has been engaged, both the screw and the mesh are secured in place. Additional screws 580 may be employed to anchor the mesh at the base of the jawbone.

In some embodiments, where the shaft is fully threaded, the mesh may be cinched around the screw head and draped over the graft site. In other embodiments, the shaft may be partially threaded such that the threading initiates at the tip but stops at some point prior to reaching the head. In either case, enough threading should be provided so that the screw may be anchored into the jawbone and stability may be attained. Typically, stability is attained after engagement of 3 mm to 4 mm of the bone.

In some embodiments, the jawbone is prepared using conventional surgical procedures and the device can be inserted in accordance with the conventional means.

The specific dimensions of each screw described herein may vary depending on the requirements of the particular application or the necessitated procedure.

Therapeutic Agents

Various embodiments of the implantable screw can be mixed, sprayed and/or coated with one or more therapeutic agents to provide an effective amount of the therapeutic agent. Alternatively, the therapeutic can be coated or impregnated on a carrier. In that case, the screw may be passed through the carrier or the carrier may be packed around the screw.

Therapeutic agents include, but are not limited to, analgesics, anti-inflammatory agents, anti-infective agents, antibiotics, bisphosphonates or other anti-resorptive agents (e.g., calcitonin), and/or growth factors. Bisphosphonates include, but are not limited to, pamidronate, alendronate, zolendronate, 3-(N,N-dimethylamino)-1-hydroxypropane-1,1-diphosphonic acid, e.g. dimethyl-APD; 1-hydroxy-ethylidene-1,1-bisphosphonic acid, e.g. etidronate; 1-hydroxy-3(methylpentylamino)-propylidene-bisphosphonic acid, (ibandronic acid), e.g. ibandronate; 6-amino-1-hydroxyhexane-1,1-diphosphonic acid, e.g. amino-hexyl-BP; 3-(N-methyl-N-pentylamino)-1-hydroxypropane-1,1-diphosphonic acid, e.g. methyl-pentyl-APD; 1-hydroxy-2-(imidazol-1-yl)ethane-1,1-diphosphonic acid, e.g. zoledronic acid; 1-hydroxy-2-(3-pyridyl)ethane-1,1-diphosphonic acid (risedronic acid), e.g. risedronate; 3-[N-(2-phenylthioethyl)-N-methylamino]-1-hydroxypropane-1,1-bishosphonic acid; 1-hydroxy-3-(pyrrolidin-1-yl)propane-1,1-bisphosphonic acid, 1-(N-phenylaminothiocarbonyl)methane-1,1-diphosphonic acid, e.g. FR 78844 (Fujisawa); 5-benzoyl-3,4-dihydro-2H-pyrazole-3,3-diphosphonic acid tetraethyl ester, e.g. U81581 (Upjohn); or 1-hydroxy-2-(imidazo[1,2-a]pyridin-3-yl)ethane-1,1-diphosphonic acid, e.g. YM 529, or combinations thereof or the like.

An effective amount of the therapeutic agent is such that when administered, the drug results in alteration of the biological activity, such as, for example, inhibition of inflammation, reduction or alleviation of pain, growth of bone, etc.

A therapeutic agent can be an analgesic. "Analgesic" refers to an agent or compound that can reduce, relieve or eliminate pain. Examples of analgesic agents include but are not limited to acetaminophen, a local anesthetic, such as for example, lidocaine, bupivicaine, ropivacaine, opioid analgesics such as buprenorphine, butorphanol, dextromoramide, dezocine, dextropropoxyphene, diamorphine, fentanyl, alfentanil, sufentanil, hydrocodone, hydromorphone, ketobemidone, levomethadyl, levorphanol, mepiridine, methadone, morphine, nalbuphine, opium, oxycodone, papaveretum, pentazocine, pethidine, phenoperidine, piritramide, dextropropoxyphene, remifentanil, sufentanil, tilidine, tramadol, codeine, dihydrocodeine, meptazinol, dezocine, eptazocine, flupirtine or a combination thereof.

The phrase "anti-inflammatory agent" refers to an agent or compound that has anti-inflammatory effects. These agents may remedy pain by reducing inflammation. Examples of anti-inflammatory agents include, but are not limited to, a statin, sulindac, sulfasalazine, naroxyn, diclofenac, indomethacin, ibuprofen, flurbiprofen, ketoprofen, aclofenac, aloxiprin, aproxen, aspirin, diflunisal, fenoprofen, mefenamic acid, naproxen, phenylbutazone, piroxicam, meloxicam, salicylamide, salicylic acid, desoxysulindac, tenoxicam, ketoralac, clonidine, flufenisal, salsalate, triethanolamine salicylate, aminopyrine, antipyrine, oxyphenbutazone, apazone, cintazone, flufenamic acid, clonixeril, clonixin, meclofenamic acid, flunixin, colchicine, demecolcine, allopurinol, oxypurinol, benzydamine hydrochloride, dimefadane, indoxole, intrazole, mimbane hydrochloride, paranylene hydrochloride, tetrydamine, benzindopyrine hydrochloride, fluprofen, ibufenac, naproxol, fenbufen, cinchophen, diflumidone sodium, fenamole, flutiazin, metazamide, letimide hydrochloride, nexeridine hydrochloride, octazamide, molinazole, neocinchophen, nimazole, proxazole citrate, tesicam, tesimide, tolmetin, triflumidate, fenamates (mefenamic acid, meclofenamic acid), nabumetone, celecoxib, etodolac, nimesulide, apazone, gold, tepoxalin; dithiocarbamate, or a combination thereof. Anti-inflammatory agents also include other compounds such as steroids, such as for example, fluocinolone, cortisol, cortisone, hydrocortisone, fludrocortisone, prednisone, prednisolone, methylprednisolone, triamcinolone, betamethasone, dexamethasone, beclomethasone, fluticasone interleukin-1 receptor antagonists, thalidomide (a TNF-α release inhibitor), thalidomide analogues (which reduce TNF-α production by macrophages), bone morphogenetic protein (BMP) type 2 or BMP-4 (inhibitors of caspase 8, a TNF-α activator), quinapril (an inhibitor of angiotensin II, which upregulates TNF-α), interferons such as IL-11 (which modulate TNF-α receptor expression), and aurin-tricarboxylic acid (which inhibits TNF-α), guanidinoethyldisulfide, or a combination thereof.

Exemplary anti-inflammatory agents include, for example, naproxen; diclofenac; celecoxib; sulindac; diflunisal; piroxicam; indomethacin; etodolac; meloxicam; ibuprofen; ketoprofen; r-flurbiprofen; mefenamic; nabumetone; tolmetin, and sodium salts of each of the foregoing; ketorolac bromethamine; ketorolac tromethamine; ketorolac acid; choline magnesium trisalicylate; rofecoxib; valdecoxib; lumiracoxib; etoricoxib; aspirin; salicylic acid and its sodium salt; salicylate esters of alpha, beta, gamma-tocopherols and tocotrienols (and all their d, 1, and racemic isomers); methyl, ethyl, propyl, isopropyl, n-butyl, sec-butyl, t-butyl, esters of acetylsalicylic acid; tenoxicam; aceclofenac; nimesulide; nepafenac; amfenac; bromfenac; flufenamate; phenylbutazone, or a combination thereof.

Exemplary steroids include, for example, 21-acetoxypregnenolone, alclometasone, algestone, amcinonide, beclomethasone, betamethasone, budesonide, chloroprednisone, clobetasol, clobetasone, clocortolone, cloprednol, corticosterone, cortisone, cortivazol, deflazacort, desonide, desoximetasone, dexamethasone, dexamethasone 21-acetate, dexamethasone 21-phosphate di-Na salt, diflorasone, diflucortolone, difluprednate, enoxolone, fluazacort, flucloronide, flumethasone, flunisolide, fluocinolone acetonide, fluocinonide, fluocortin butyl, fluocortolone, fluorometholone, fluperolone acetate, fluprednidene acetate, fluprednisolone, flurandrenolide, fluticasone propionate, formocortal, halcinonide, halobetasol propionate, halometasone, halopredone acetate, hydrocortamate, hydrocortisone, loteprednol etabonate, mazipredone, medrysone, meprednisone, methylprednisolone, mometasone furoate, paramethasone, prednicarbate, prednisolone, prednisolone 25-diethylamino-acetate, prednisolone sodium phosphate, prednisone, prednival, prednylidene, rimexolone, tixocortol, triamcinolone, triamcinolone acetonide, triamcinolone benetonide, triamcinolone hexacetonide or a combination thereof.

In various embodiments, the therapeutic agent can comprise BMPs and/or CDMPs including, but not limited to, BMP-2, BMP-4, BMP-6, BMP-7, BMP-8, and CDMP-1.

Anti-infective agents to treat infection include by way of example and not limitation, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Other exemplary antibacterial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefmenoxime hydrochloride; cefmetazole; cefmetazole sodium; cefonicid monosodium; cefonicid sodium; cefoperazone sodium; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodium; nafcillin sodium; nalidixate sodium; nalidixic acid; natainycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine;

sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In various embodiments, the implantable screw comprises material, such as for example, polyurethane, polyurea, polyether(amide), PEBA, thermoplastic elastomeric olefin, copolyester, and styrenic thermoplastic elastomer, steel, aluminum, stainless steel, titanium, zirconium, carbon, metal alloys with high non-ferrous metal content and a low relative proportion of iron, carbon fiber, glass fiber, plastics, ceramics or combinations thereof.

In various embodiments, the screw comprises biopolymers including but not limited to poly(alpha-hydroxy acids), poly(lactide-co-glycolide) (PLGA), polylactide (PLA), polyglycolide (PG), polyetheretherketone (PEEK), polyethylene glycol (PEG) conjugates of poly(alpha-hydroxy acids), polyorthoesters, polyaspirins, polyphosphagenes, collagen, starch, pre-gelatinized starch, hyaluronic acid, chitosans, gelatin, alginates, albumin, fibrin, vitamin E analogs, such as alpha tocopheryl acetate, d-alpha tocopheryl succinate, D,L-lactide, or L-lactide, ,-caprolactone, dextrans, vinylpyrrolidone, polyvinyl alcohol (PVA), PVA-g-PLGA, PEGT-PBT copolymer (polyactive), methacrylates, poly(N-isopropylacrylamide), PEO-PPO-PEO (pluronics), PEO-PPO-PAA copolymers, PLGA-PEO-PLGA, PEG-PLG, PLA-PLGA, poloxamer 407, PEG-PLGA-PEG triblock copolymers, SAIB (sucrose acetate isobutyrate) or combinations thereof.

In other embodiments the screw comprises "resorbable" materials of either synthetic or natural origin. Such materials are degraded through either enzymatic, hydrolytic or other chemical reactions or cellular processes into by-products which are either integrated into, or expelled from, the body. Resorbable materials include, but are not limited to cortical bone, ceramic (e.g., hydroxyapatite, tricalcium phosphate, bioglasses, calcium sulfate, etc.) tyrosine-derived polycarbonate poly (DTE-co-DT carbonate), in which the pendant group via the tyrosine—an amino acid—is either an ethyl ester (DTE) or free carboxylate (DT) or combinations thereof. Some embodiments may include the use of all resorbable materials, all non-resorbable materials or a combination of some resorbable materials and some non-resorbable materials. The term "resorbable" encompasses materials considered "bioresorbable", "absorbable" and "bioabsorbable."

Sterilization

The implantable screws may be sterilizable. In various embodiments, one or more screws may be sterilized by radiation in a terminal sterilization step in the final packaging. Terminal sterilization of a product provides greater assurance of sterility than from processes such as an aseptic process, which require individual product components to be sterilized separately and the final package assembled in a sterile environment.

Typically, in various embodiments, gamma radiation is used in the terminal sterilization step, which involves utilizing ionizing energy from gamma rays that penetrates deeply in the device. Gamma rays are highly effective in killing microorganisms, they leave no residues nor have sufficient energy to impart radioactivity to the device. Gamma rays can be employed when the device is in the package and gamma sterilization does not require high pressures or vacuum conditions, thus, package seals and other components are not stressed. In addition, gamma radiation eliminates the need for permeable packaging materials.

In various embodiments, electron beam (e-beam) radiation may be used to sterilize one or more components of the device. E-beam radiation comprises a form of ionizing energy, which is generally characterized by low penetration and high-dose rates. E-beam irradiation is similar to gamma processing in that it alters various chemical and molecular bonds on contact, including the reproductive cells of microorganisms. Beams produced for e-beam sterilization are concentrated, highly-charged streams of electrons generated by the acceleration and conversion of electricity.

Other methods may also be used to sterilize one or more components of the device, including, but not limited to, gas sterilization, such as, for example, with ethylene oxide or steam sterilization.

Kits

In various embodiments, an implantable device may be packaged in a kit in order to maintain the device in a sterile environment before it is implanted. In various embodiments, a kit is provided comprising one or more implantable screws. The kit may include additional parts combined together with the implantable screw to be used to implant the screw. The kit may include the implantable screw(s) in a first compartment. The second compartment may include instruments needed for implanting the screw (such as for example, implantation tool, driver, etc.). A third compartment may include gloves, drapes, wound dressings and other procedural supplies for maintaining sterility of the implanting process, as well as an instruction booklet. A fourth compartment may include additional needles and/or sutures. In a fifth compartment, the kit may include osteoinductive and/or osteoconductive agents (e.g., BMP) for application into the space created by the contoured head. Each tool may be separately packaged in a plastic pouch that is radiation sterilized. A cover of the kit may include illustrations of the implanting procedure and a clear plastic cover may be placed over the compartments to maintain sterility.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed:

1. An implantable screw for maintaining space during bone grafting procedures in a patient in need of such treatment, the implantable screw comprising: a contoured head having a highly-polished, machined surface, a region adapted to support soft tissue and to shield a bone graft area from compressive forces, and a curved under surface to increase capacity for bone growth; a threaded shaft for anchoring the screw in the bone, wherein the outer diameter of the shaft is about 1.4 mm or less and the inner diameter of the shaft is about 1.2 mm or less, and the inner diameter is less than the outer diameter; and a tip adapted to penetrate bone tissue, wherein the screw is removable after new host bone is generated.

2. An implantable screw of claim 1, wherein the screw comprises titanium.

3. An implantable screw of claim 1, wherein the contoured head ranges in size from about 3 mm to about 7 mm.

4. An implantable screw of claim 1, wherein the length of the shaft ranges from about 8 mm to about 17 mm and wherein the threading pitch allows the screw to stabilize in bone after engagement of about 3 mm to about 4 mm of bone.

5. An implantable screw of claim 1, wherein the shaft is threaded on the apical coronal regions so the entire length of the shaft is threaded or less than the entire length of the shaft is threaded.

6. An implantable screw of claim 1, wherein the screw is implanted into the bone tissue and the bone tissue further comprises a second implantable screw.

7. An implantable screw of claim 1, wherein the screw is coated with a material for growing bone.

8. An implantable screw of claim 1, wherein the screw supports incorporation of bone graft material.

9. An implantable screw of claim 1, further comprising a mesh or a membrane or a collagen sponge having BMP-2 disposed in or on the sponge, wherein the threaded shaft engages the mesh, membrane or sponge.

10. An implantable screw of claim 1, wherein the screw comprises a tip adapted for self-drilling.

11. An implantable device for maintaining space during bone grafting procedures in a patient in need of such treatment, the implantable device comprising: at least a first screw and a second screw, wherein each of the first screw and the second screw comprise a contoured head having a highly-polished, machined surface, a region adapted to support soft tissue and to shield a bone graft area from compressive forces, and a curved under surface to increase capacity for bone growth, a threaded shaft for anchoring the screw in the bone, and a tip adapted to penetrate bone tissue; wherein the head of the first screw is adjacent to the head of the second screw, and wherein the device is removable after new host bone is generated.

12. An implantable device of claim 11 wherein at least the first screw comprises titanium.

13. An implantable device of claim 11 wherein the head of each of the first screw and the second screw range in size from about 3 mm to about 7 mm and the region of the contoured head of the first screw and the second screw each comprise a curved under surface to increase capacity for bone growth.

14. An implantable device of claim 11 wherein the head of the first screw is a different size than the head of the second screw.

15. An implantable device of claim 11 wherein the outer shaft of each of the first screw and the second screw has a diameter of about 1.4 mm or less and an inner diameter of the shaft of each of the first screw and the second screw is about 1.2 mm or less, and the inner diameter is less than the outer diameter.

16. An implantable device of claim 11 wherein the outer or inner diameter of the shaft size of the first screw is different from the outer or inner diameter of the shaft size of the second screw.

17. An implantable device of claim 11 wherein the length of the shaft of each of the first and second screw ranges from about 8 mm to about 17 mm.

18. An implantable device of claim 11 wherein the length of the shaft of the first screw is different from the length of the shaft of the second screw.

19. An implantable screw of claim 11, wherein the screw supports bone graft material.

20. A method of grafting bone in an oral procedure comprising: implanting into the jawbone an implantable device comprising at least one implantable screw, the screw comprising a contoured head having a highly-polished, machined surface, a region adapted to support soft tissue and to shield a bone graft area from compressive forces, and a curved under surface to increase capacity for bone growth, further wherein the contoured head ranges in size from about 3 mm to about 7 mm, a threaded shaft for anchoring the screw in the bone, wherein the outer diameter of the shaft is about 1.4 mm or less and the inner diameter of the shaft is about 1.2 mm or less, and the inner diameter is less than the outer diameter, and a tip adapted to penetrate bone tissue; incorporating a bone growth material on or near the screw; and removing the implantable device once new host bone has been generated.

* * * * *